US012551215B2

(12) United States Patent
Sejor et al.

(10) Patent No.: US 12,551,215 B2

(45) Date of Patent: Feb. 17, 2026

(54) APPARATUS AND METHOD FOR FORMING AN ANASTOMOSIS

(71) Applicant: BariaTek Medical, Paris (FR)

(72) Inventors: Eric Sejor, Nice (FR); Youssef Biadillah, Maisons-Laffitte (FR); Yonatan Gray, Paris (FR); Christophe Naz, Fontainebleau (FR); Thomas Friedrich, Dresden (DE); Mario Heintze, Dresden (DE); Tobias Rokosch, Dresden (DE)

(73) Assignee: Baria Tek Medical, Paris (FR)

( * ) Notice: Subject to any disclaimer, the term of this patent is extended or adjusted under 35 U.S.C. 154(b) by 108 days.

(21) Appl. No.: 18/563,070

(22) PCT Filed: Jun. 21, 2022

(86) PCT No.: PCT/EP2022/066887
§ 371 (c)(1),
(2) Date: Nov. 21, 2023

(87) PCT Pub. No.: WO2022/268816
PCT Pub. Date: Dec. 29, 2022

(65) Prior Publication Data

US 2024/0237984 A1 Jul. 18, 2024

(30) Foreign Application Priority Data

Jun. 22, 2021 (EP) .................................... 21315101

(51) Int. Cl.
*A61B 17/11* (2006.01)
*A61B 17/00* (2006.01)

(52) U.S. Cl.
CPC ..... *A61B 17/11* (2013.01); *A61B 2017/00867* (2013.01); *A61B 2017/00876* (2013.01)

(58) Field of Classification Search
CPC ....... A61B 17/00; A61B 17/11; A61B 17/115; A61B 17/12045; A61B 2017/00867; A61B 2017/00876
See application file for complete search history.

(56) References Cited

U.S. PATENT DOCUMENTS 10,154,844 B2 * 12/2018 Sharma ................ A61B 17/122
2007/0038293 A1 * 2/2007 St.Goar ............ A61B 17/00234 623/2.11

FOREIGN PATENT DOCUMENTS

WO 2017/203523 A1 11/2017
WO 2018/057613 A2 3/2018

OTHER PUBLICATIONS

International Search Report Corresponding to PCT/EP2022/066887 mailed Oct. 4, 2022.

(Continued)

*Primary Examiner* — Vi X Nguyen
(74) *Attorney, Agent, or Firm* — Finch & Maloney PLLC

(57) ABSTRACT

Apparatus for forming an anastomosis between first and second body lumen wall sections, the apparatus having a coil implant (10) which has an elongate tubular member (16) made of shape memory material, the elongate member being self-expanding from a stretched-out stowed configuration for introduction into the body, to an implantation configuration in which a first portion (12) of the elongate member forms at least a first loop (20) of the coil and a second portion (14) of the elongate member forms at least a second loop (22) of the coil, the elongate member having at least one interior cavity, the coil implant further having a plurality of magnets (24) carried by the first and second portions of the elongate member, each magnet of the plurality being at least partly accommodated within the at least one interior cavity of the elongate member, the magnets arranged such that the first loop is magnetically attracted to the second loop (Continued)

for creating a magnetic compression anastomosis in tissue trapped between the first and second loops. The loops may have spirals with tailored compression forces and/or tailored flexibility.

20 Claims, 9 Drawing Sheets

(56) References Cited

OTHER PUBLICATIONS

Written Opinion Corresponding to PCT/EP2022/066887 mailed Oct. 4, 2022.

* cited by examiner

APPARATUS AND METHOD FOR FORMING AN ANASTOMOSIS

FIELD OF THE INVENTION

The present invention relates to the field of anastomosis formation between body lumina. Non-limiting aspects of the invention relate to forming an anastomosis in a patient's digestive system, preferably in the gastrointestinal tract; and/or to formation of a magnetic compression anastomosis.

BACKGROUND TO THE INVENTION

An anastomosis is a surgical cross-connection between two different sections of body lumen. The gastrointestinal tract is the luminal route in the body from the esophagus to the anus. Anastomoses formed somewhere along or in the gastrointestinal tract are one form of therapy used to treat digestion-related problems, such as diabetes, obesity, bowel diseases and obstructions. Although an anastomosis can be formed by an open-surgery procedure, significant technical challenges remain in achieving anastomoses equally effectively by minimally invasive procedures, for example, laparoscopically, endoscopically or endoluminally.

U.S. Pat. No. 10,154,844 teaches an anastomosis device including magnets coupled to the exterior of a wire capable of changing shape from a straight wire into a coil when deployed in the body. The coil is said to exert compressive force upon layers of tissue caught between loops of the coil. The compressive force is enhanced by attractive forces between magnets coupled with adjacent loops of the coil and causes the coil to cut through the tissue layers, creating an anastomosis. One end of the wire is said preferably to be provided with a connecting member, such as a screw or a nut, for connecting with a delivery device.

It would be desirable to address several of the shortcoming of prior anastomosis devices.

SUMMARY OF THE INVENTION

Aspects of the invention are defined in the claims.

Additionally or alternatively, one aspect of the invention provides apparatus for forming an anastomosis between first and second body lumen wall sections, optionally in a patient's digestive system, further optionally in the gastrointestinal tract.

The apparatus comprises first and second elongate member portions comprising, e.g. made from, shape memory material. The first and second elongate member portions are self-expandable from a stretched-out stowed configuration for introduction into the body, to an implantation configuration in which the first elongate member portion forms a first loop, and the second elongate member portion forms a second loop. At least one, optionally both, of the elongate member portions comprises at least one interior cavity within the elongate member portion.

The apparatus further comprises a plurality of magnets carried by the first and second elongate member portions. At least one, optionally some, optionally all, of this plurality of magnets is at least partly accommodated within the at least one cavity of a respective elongate member portion. The magnets can be arranged such that the first loop is magnetically attracted to the second loop for creating a magnetic compression anastomosis in tissue trapped between the first and second loops.

In some embodiments, the apparatus comprises a coil implant, the first and second elongate member portions being respective portions of an elongate member forming both portions. Optionally, the elongate member is a monolithic body.

Accommodating magnets at least partly in one or more cavities of an elongate member portion can provide several advantages. For example, it can facilitate providing the apparatus with a more streamlined shape, compared to externally mounted or externally carried magnets. A streamlined shape may have several benefits. A streamlined shape can assist in trouble-free deployment of the apparatus (e.g. coil device) from a delivery device. A streamlined shape can also assist in evacuation of the apparatus (e.g. coil device) from the body after the anastomosis has formed. For example, in the case of the gastrointestinal tract, the apparatus (e.g. coil device) may separate from the intestine wall, and advance in the intestine with fecal matter to pass through the patient's anus. A streamlined shape can reduce risk of blockage or injury or discomfort for the patient.

Additionally or alternatively, accommodating magnets at least partly in one or more cavities of an elongate member portion can provide a convenient way of mounting the magnets in the apparatus. It can also assist in protecting the magnets from external damage.

In some embodiments, at least two of the magnets can be accommodated, at least partly, within the same cavity of an elongate member portion. The elongate member portion may comprise a tube, and the cavity can include a hollow interior of the tube.

A tubular form of elongate member or elongate member portion can provide more structural support than, for example, a wire, as well as providing cavity space for accommodating, at least partly, one or more of the magnets.

Whatever the form of elongate member or elongate member portion, the elongate member may comprise apertures or windows spaced apart along its length.

At least some of the magnets may be arranged at and/or in at least some of the apertures. The apertures may, for example, permit magnets to be accommodated that do not fit entirely within the interior hollow of a tube, and/or to be fitted in an orientation that does not fit entirely with the interior hollow of a tube. If the elongate member is non-tubular, the apertures may provide cavities for accommodating, at least partly, the magnets.

A closely related second aspect of the invention, optionally in combination with any of the features of the first aspect, provides apparatus for forming an anastomosis between first and second body lumen wall sections, optionally in a patient's digestive system, further optionally in the gastrointestinal tract.

In the second aspect, the apparatus comprises first and second elongate member portions comprising, e.g. made from, shape memory material. The first and second elongate member portions are self-expandable from a stretched-out stowed configuration for introduction into the body, to an implantation configuration in which the first elongate member portion forms a first loop, and the second elongate member forms a second loop. At least one, optionally both, of the elongate member portions comprises a tube.

The coil implant further comprises a plurality of magnets carried by the first and second elongate member portions, the magnets arranged such that the first turn is magnetically attracted to the second turn for creating a magnetic compression anastomosis in tissue trapped between the first and second turns.

In some embodiments, the apparatus comprises a coil implant, the first and second elongate member portions being respective portions of an elongate member forming both portions. Optionally, the elongate member is a monolithic body.

A closely related third aspect of the invention, optionally in combination with any of the features of the first and/or second aspect, provides apparatus for forming an anastomosis between first and second body lumen wall sections, optionally in a patient's digestive system, further optionally in the gastrointestinal tract.

In the third aspect, the apparatus comprises first and second elongate member portions comprising, e.g. made from, shape memory material. The first and second elongate member portions are self-expandable from a stretched-out stowed configuration for introduction into the body, to an implantation configuration in which the first elongate member portion forms a first loop, and the second elongate member forms a second loop. At least one of the loops comprises a first segment and a second segment, optionally collectively defining a loop in the form of a spiral in the implantation configuration, the first segment being at least partly closer to the central axis of the spiral than the second segment. The spiral may optionally be generally planar in a direction generally orthogonal to a central axis of the apparatus.

The coil implant further comprises a plurality of magnets carried by the first and second elongate member portions, the magnets arranged such that the first loop is magnetically attracted to the second loop for creating a magnetic compression anastomosis in tissue trapped between the first and second loops.

In the third aspect, the apparatus is configured such that:

(i) the second segment is more flexible, in at least one direction of flexibility, than first segment; and/or (ii) the second segment is configured to apply a smaller compression force to underlying tissue than the first segment.

In some embodiments, the second segment may be both more flexible and configured to apply a smaller compression force.

Application of a smaller compression force by the second segment, if used, enables the compression effect on the tissue wall sections to be tailored to assist in anastomosis formation. The compression force can be concentrated at a first tissue zone corresponding to the first segment of the loop, leading to tissue necrosis by which the anastomosis is created. The smaller compression force in a second tissue zone corresponding to the second segment may be radially outwardly of, and surround, the first zone. The smaller compression force may press tissue wall section together in the second zone, to urge fusion of tissue as part of the healing effect, but optionally without necrosis in the second zone. This can lead to a radially thick band of joined tissue around the anastomosis.

In some embodiments, both the first and second loops each include respective first and segments.

Such a configuration can broaden the area of the tissue join with the aim of further ensuring a reliably continuous join around the entirety of the anastomosis. The process of tissue necrosis and healing by which the anastomosis is created is a biological process triggered by the compression forces. Different patients may experience different rates of tissue necrosis, healing and tissue fusion, leading to some variation in anastomosis formation from one patient to another. Furthermore, although the biological process is expected to be uniform around a closed loop shape, variation may occur in some cases. For example, the join may be naturally thicker in one region than another. Such biological variations may be exacerbated by patient conditions, such as diabetes. Providing the second segment for pressing tissue with a lesser compression force, can assist the biological process of joining tissues together with sufficient or enhanced radial thickness, to mitigate against such variations, and create a robust, leak-free join.

In some embodiments, the magnets may be carried, at least principally, by the first segment (s). Optionally, the second segment (s) carries no magnets.

The flexibility of the second segment (s) may also be configured to determine whether the apparatus will separate from the wall tissues once the anastomosis has formed, or whether the second segments may retain the apparatus captive with respect to the tissue walls. A relatively flexible second segment may be configured not to retain the apparatus captive, by bending or deforming to allow the apparatus to pass through the smaller aperture of the created anastomosis. A relatively stiff second segment may be configured to resist bending, and thereby retain the apparatus captive.

In some embodiments, the apparatus comprises a coil implant, the first and second elongate member portions being respective portions of an elongate member forming both portions. Optionally, the elongate member is a monolithic body.

In any of the above aspects, apertures and/or cuts in the elongate member or elongate member portion may provide enhanced flexibility. This is especially, but not exclusively, advantageous for one or more elongate member portions comprising a tube.

Optionally, such cuts and/or apertures are formed in one or more surface regions selected to enhance flexibility in a plane perpendicular to a central axis of the coil in the implanted configuration. For example, the one or more surface regions may be or include: (i) a surface region of the elongate member portion that faces radially inwardly towards a central axis of the coil in the implantation configuration, and/or (ii) a surface region of the elongate member portion that faces radially outwardly away from a central axis of the coil in the implantation configuration.

At least some of the apertures and/or cuts, whether provided to enhance flexibility and/or to accommodate at least partly the magnets, may communicate with a hollow interior of the elongate member or portion.

In any aspect above, at least one, optionally both of the elongate member portions may be configured to provide, in the implanted configuration, one or more of:

a) A loop extending at least 80%, optionally at least 90%, of a complete turn around the central axis of the loop;

b) A loop extending at least 1 complete turn around the central axis;

c) A loop extending at least 1.8, optionally at least 1.9, complete turns around the axis of the coil;

d) A loop extending at least two complete turns around the central axis;

e) A loop extending at least 2.5 complete turns around the central axis, optionally at least 2.8 complete turns, optionally at least 2.9 complete turns, optionally at least 3.0 complete turns f) A loop extending less than 1 complete turn around the central axis of the loop. For example, the loop may include a circumferential discontinuity and/or gap.

Optionally, at least one of the first and second elongate member portions comprises a generally planar spiral shape of more than one turn. One turn, optionally a radially innermost turn, may have a greater rigidity than another turn (or at least partial turn) in the spiral.

In addition to the advantages already discussed above, providing an outer turn of the spiral that is more flexible than an inner turn can facilitate deployment from the delivery device. The implant comprises shape memory material that is self-expanding to the implanted configuration. In use, the implant can be allowed by the delivery device to self-expand progressively from one end. By making a final portion of the device relatively flexible, there is less tendency for the implant to spring free or jump free when only a small part of the implant remains under control of the delivery device.

As used herein, the term "loop" includes any form resembling a partial or complete shape extending around a central region. The loop may be generally circular, or non-circular. The loop may be generally curved, and/or comprise rectilinear segments or sides. The loop may be a closed loop shape, or it may be a non-closed loop. The loop may have a spiral form (whether a generally circular spiral or a generally non-circular spiral, such as a rectilinear spiral).

As used herein the term "turn" refers to an angular extent of the loop around a central axis of the first and/or second portion (or the apparatus as a whole) in the implantation configuration, whether or not the loop is circular. A complete turn refers to an angular extent of 360°.

Additionally or alternatively to any of the above, in either of the above aspects, the elongate member may further comprise a bridging section between the first and second portions, the bridging section not carrying a magnet. The bridging section may be continuous with the first and/or second portions.

In some embodiments, in the implantation configuration, the first turn is defined generally in a first plane, the second turn is defined generally in a second plane, and the bridging section extends between the first and second planes, optionally wherein first plane is generally perpendicular to the axis of the coil, and/or optionally wherein the second plane is generally perpendicular to the axis of the coil.

In the implantation configuration, the bridging section may be generally inclined with respect to the first and second portions of the elongate member.

Additionally or alternatively to any of the above, the apparatus may further comprise a sleeve of flexible material covering the elongate member and/or the magnets. The sleeve may serve to at least partly hold the magnets in position. For example, the sleeve may fit tightly around the elongate member. Additionally or alternatively, the sleeve may provide a lubricious surface. For example, the sleeve may be made of PTFE. Such a sleeve can be applied by heat-shrinking the sleeve around the elongate member.

A further aspect of the invention provides a method of forming an anastomosis between first and second body lumen wall sections, comprising:

a. providing a coil implant (10) comprising an elongate member (16) made of shape memory material, the elongate member comprising first and second portions (12, 14), and the implant further comprising a plurality of magnets (24) carried by the first and second portions of the elongate member;
b. introducing the implant to a target site for the anastomosis with the elongate member in a stretched-out stowed configuration;
c. causing the elongate member to self-expand to an implantation configuration in which the first portion (12) of the elongate member forms at least a first loop (20) of the coil and a second portion (14) of the elongate member forms at least a second loop (22) of the coil, the magnets arranged such that the first loop is magnetically attracted to the second loop for creating a magnetic compression anastomosis in tissue trapped between the first and second loops.

In some embodiments, the step of providing may comprise providing the elongate member in the form of a tube. Additionally or alternatively, the step of providing may comprising providing the plurality of magnets such that each magnet of the plurality is at least partly accommodated within at least one interior cavity of the elongate member.

In any of the above aspects, at least one (optionally both) of the first and second elongate member portions may be configured to coil when transitioning from the stretched-out stowed configuration to the implantation configuration. The action of coiling means that the respective portion winds and/or curls at least partly around an axis to form the respective loop in the implantation configuration. In some embodiments, the respective portion may coil from a non-loop shape (e.g. from a generally linear stretched out configuration) into the loop shape. For example, the loop may be formed only when in the deployed configuration.

Additionally or alternatively, in any of the above aspects, at least one (optionally both) of the first and second elongate member portions my at least partly wind, and/or be at least partly wound, around an axis, at least in the implantation configuration. In some embodiments, the respective portion may wind from a non-loop shape (e.g. from a generally liner stretched out configuration) into the loop shape. For example, the loop may be formed only when in the deployed configuration.

Additionally or alternatively, in any of the above aspects including a bridging section, the diameter of the first elongate member portion, the second elongate member portion, and the bridging portion, may be substantially the same as each other, at least in the implantation configuration, and optionally in the stowed configuration.

Additionally or alternatively, in any of the above aspects including a bridging section, at least one (optionally both) of the first and second elongate member portions may comprise a circumferential discontinuity where the respective elongate member portion bends into, or bends to form, the bridging section.

In any of the above aspects, the apparatus or a component of the apparatus may optionally be formed by three-dimensional printing.

Although certain aspects, features and advantages have been highlighted above, protection is claimed for any novel feature or idea described herein and/or illustrated in the drawings, whether or not emphasis has been placed thereon.

DETAILED DESCRIPTION OF PREFERRED EMBODIMENTS

Figure 1:
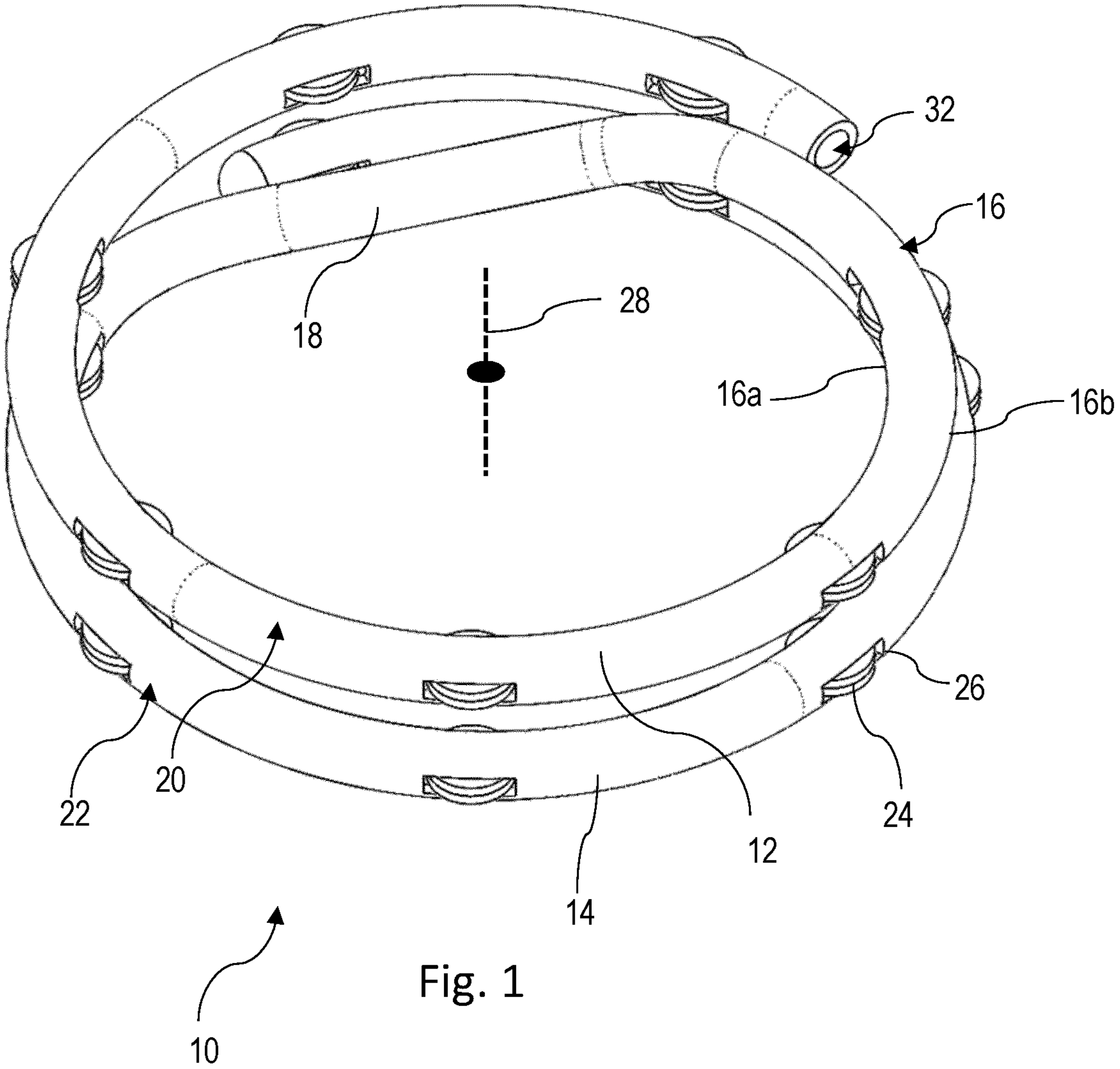
FIG. 1 is a schematic perspective view from above of a first embodiment of anastomosis coil implant in its implantation configuration.
Figure 2:
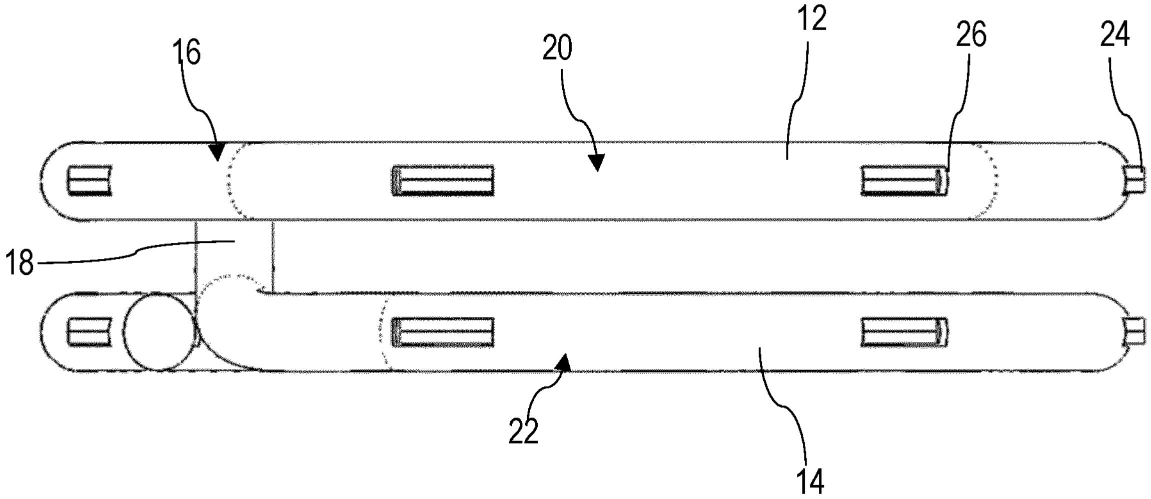
FIG. 2 is a schematic side view of the coil implant of FIG. 1, viewed from a first direction.
Figure 3:
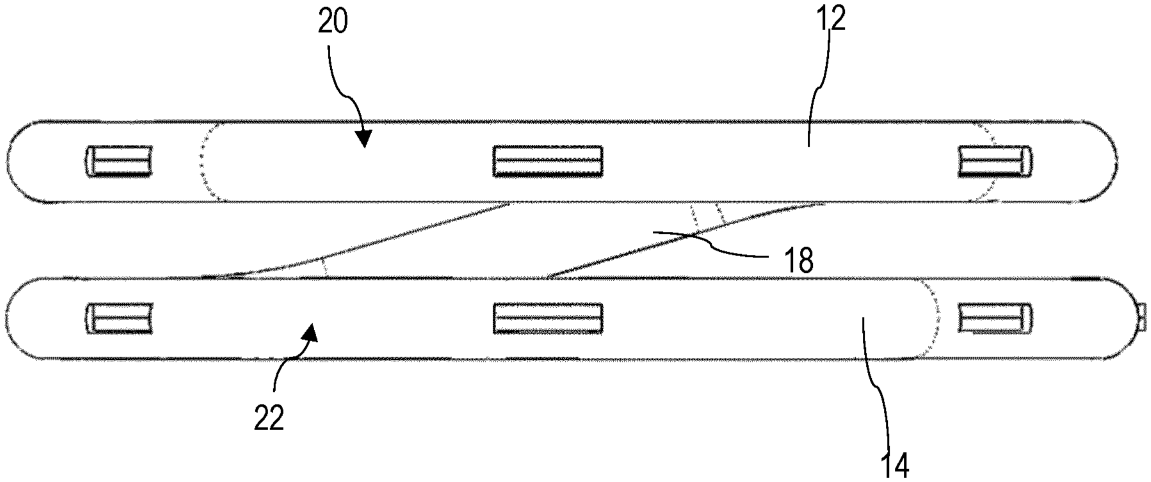
FIG. 3 is a schematic side view similar to FIG. 2, but viewed from a second orthogonal direction.

Non-limiting embodiments of the invention are now described, by way of example only, with reference to the accompanying drawings. In the different drawings, the same reference numerals are used to denote the same or equivalent features, whether or not described in detail. Features of one embodiment may be combined with another, whether or not described in detail.

Referring to the drawings, several embodiments of apparatus for forming an anastomosis are illustrated in the form of a coil implant 10. The implant 10 may be suitable for use to form an anastomosis within the digestive system of a patient, optionally in the gastro-intestinal tract.

The coil implant 10 comprises a first elongate member portion 12 and a second elongate member portion 14, made of shape memory material, optionally a shape memory alloy, for example, an alloy containing nickel and titanium, such as NiTi (e.g. nitinol) or NiTiCo. In the illustrated embodiments, the first and second elongate member portions 12 and 14 are formed as portions of the same elongate member 16, which may be a monolithic body. The elongate member 16 optionally further comprises a bridging section 18 between the first and second portions 12 and 14, as described later.

The coil implant 10 is self-expandable from a stowed configuration for introduction into a patient's body, to a deployed or implantation configuration. In the stowed configuration (e.g. FIG. 9) the first and second portions 12 and 14 are generally stretched out to a linear or near linear shape suitable for introduction using a narrow delivery device or sheath (not shown). In use, the implant is released or ejected from the delivery device or sheath to assume the implantation configuration. In the implantation configuration (e.g. FIGS. 1 to 8), the first portion 12 expands to form at least a first loop 20, and the second portion 14 expands to form at least a second loop 22 generally parallel and in register with the first loop 20. At least one, optionally both, of the first and second portions 12 and 14 is/are configured to coil and/or wind at least partly around an axis, when changing from the stowed configuration to the implantation configuration.

The coil implant 10 further comprises a plurality of magnets 24 carried by the first and second portions 12 and 14. The magnets 24 are arranged such that magnets on each portion 12, 14 create magnetic attraction between the two loops 20, 22.

In use, when the coil implant 10 is deployed across two adjacent body lumen wall sections, with one loop 20 on one side of the wall sections and the other loop 22 on the other side sandwiching the wall tissues between the loops 20 and 22, the magnetic attraction compresses the tissues, leading to necrosis, and within a matter of weeks, resulting in biological creation of an anastomosis. The compression forces are distributed around a substantially complete loop shape by means of the elongate member portions 12 and 16 in contact with the tissue.

A feature of some embodiments described herein is that at least one, optionally both, of the portions 12 and 14 has at least one interior cavity 32, and at least some of the magnets 24 are accommodated, at least partly, within the (at least one) cavity 32.

The embodiments illustrate the elongate member 16 in the form of a tube. The elongate member 16 is made from tubular stock of shape memory material, heat-processed to adopt the implantation configuration. The interior hollow of the tube forms at least part of the cavity for accommodating, at least partly, at least some of the magnets 24. Additionally or alternatively, whether or not the elongate member 16 is tubular, the elongate member 16 comprises windows or apertures 26 in which and/or at which at least some of the magnets 24 are disposed. The apertures 26 may also form part of a cavity for one or more magnets 24. In the illustrated forms, each aperture 26 is associated with one magnet 24. Plural apertures 26 (e.g. on opposite surface regions of the elongate member) may be associated with the same magnet 24.

Various arrangements of apertures 26 for the magnets 24 are envisaged. For example, in the embodiment of FIGS. 1 to 4, the apertures 26 are arranged in at least one, actually both, of: (i) a surface region **16*a* (e.g. laterally inward surface region) of the elongate member 16 that faces radially inwardly towards a central axis 28 of the coil in the implantation configuration, and/or (ii) a surface region 16*b* (e.g. laterally outward surface region) of the elongate member 16 that faces radially outwardly away from a central axis 28 of the coil in the implantation configuration. In the embodiments of FIGS. 5 to 8, the apertures 26 are arranged in one or more surface regions 16*c* (e.g. upper and lower surface regions) of the elongate member 16 facing generally parallel to the central axis 28 of the coil in the implantation configuration. Combinations of such orientations of the apertures 26** are also envisaged.

The apertures 26 may be generally in the surface of the elongate member 16, or the apertures 26 may include a rim or "window frame", for example, to permit a generally flat or planar aperture in a non-flat (e.g. rounded) surface of the elongate member 16.

Referring to FIGS. 5 to 8, the magnets 24 may be generally entirely accommodated within the at least one cavity of the elongate member 16, such that the magnets 24 do not protrude substantially (optionally do not protrude at all) with respect to the surface of the elongate member. Alternatively, referring to FIGS. 1 to 4, the magnets 24 may protrude somewhat from the surface of the elongate member 16 carrying the magnets.

Whether or not magnets 24 have protruding portions, by accommodating magnets 24 at least partly with at least one cavity 32 of the elongate member 16, the coil implant 10 can benefit from streamlining of the shape or profile of the device. It can also provide a convenient way of mounting the magnets 24 to the elongate member. It can also provide at least some degree of protection for the magnets 24.

The magnets 24 may have any suitable shape, for example, one or more of: generally planar; polygonal; cylindrical; disc-shaped; rod-shaped; barrel-shaped (with inwardly tapered or inwardly turned ends). FIGS. 1-4 illustrate generally thin cylindrical or polygonal magnets 24. FIGS. 5-9 illustrate rod-shaped or barrel-shaped magnets 24. A barrel-shaped magnet may, for example, be press-fitted into an aperture or cavity and held by an interference fit, for example, at its opposite ends. In general, magnets 24 of any shape may be secured in position by any suitable technique, for example, interference fitting, welding or adhesive attachment to the elongate member 16.

In some embodiments, the combination of the elongate member 16 and the magnets 24 may be covered by a sleeve of flexible material (not shown). The sleeve may serve to at least partly hold the magnets in position in the apertures 26. For example, the sleeve may fit tightly around the elongate member 26. Additionally or alternatively, the sleeve may provide a lubricious surface. For example, the sleeve may be made of PTFE. Such a sleeve can be applied by heat-shrinking the sleeve around the elongate member 16.

Additionally or alternatively, whether or not the magnets 24 are accommodated within one or more cavities of the elongate member 16, a further feature used in some embodiments described herein is that the elongate member 16 (or at least one of the portions 12, 14, 18) is tubular. A tube can provide generally more structural support than, for example, a wire. Such structural support can provide good control over the shape of the implant 10 in the implantation configuration, and also offers the possibility of directional flexibility, as discussed later below. Structural support is advantageous especially, but not exclusively, when the coil device 10 includes relatively few loops in number, for example, three, or two or fewer loops at one or both of the first and second portions 12 and 14.

In the illustrated embodiments, the elongate member 16 is made from tubular shape memory material, optionally in hypotube form. The illustrated embodiments show a tube that is generally circular in cross-section, but other shapes are envisaged, for example, oval, or polygonal (for example, triangular, quadrilateral, rectangular, square, etc).

Use of a tubular elongate member 16 also permits the implant 10 optionally to be introduced to the implantation site over a guidewire (not shown). The magnets 24 may be arranged to provide a through-passage for the guidewire through the elongate member 16. For example, the magnets 24 may have bores (not shown) aligned internally with the interior hollow of the tube.

As mentioned above, the illustrated embodiments of coil implant 10 include a bridging section 18 extending between and/or linking the first and second portions 12 and 14. In use, when the coil device 10 is implanted across tissue walls at which the anastomosis is to be formed, the bridging section 18 passes through the tissue walls. In the illustrated forms, the first portion 12 defines an at least first loop in a first plane, the second portion 14 defines an at least second loop in a second plane, and the bridging section 18 extends from one plane to the other. The bridging section 18 is inclined with respect to these planes.

The bridging section 18 may optionally be configured to extend inwardly of the periphery of the loop shapes, in the implantation configuration. Such a configuration can avoid the bridging section 18 from interfering substantially with the circumferential shape of each loop that applies pressure to the tissue walls sandwiched between the loops. For example, referring to FIGS. 1 to 5 and 8, the bridging section 18 can form a flat of a D-shape within the profile of the loops. In these figures, the first and second portions 12 and 14 form turns extending in the same sense (e.g. both clockwise, or both anticlockwise) around the central axis 28. Referring to the further embodiment of FIGS. 6 and 7, the bridging section 18 forms an S-shape in extending between the loops, for example, crossing the central axis 28. In these figures, the first and second portions 12 and 14 form turns extending in opposite senses to each other (e.g. one clockwise, the other anticlockwise) around the central axis 28.

In the illustrated embodiments, the loop shape formed by at least one, optionally both, of the first and second portions 12 and 14 includes a circumferential discontinuity, for example where the respective first and/or second portion 12/14 bends into, or bends to form, the bridging section 18.

In the illustrated embodiments, the diameter of the elongate member 16 may be substantially the same in the first section 12, the second section 14 and the bridging section 18, at least in the implantation configuration, and optionally also in the stowed configuration.

Figure 8:
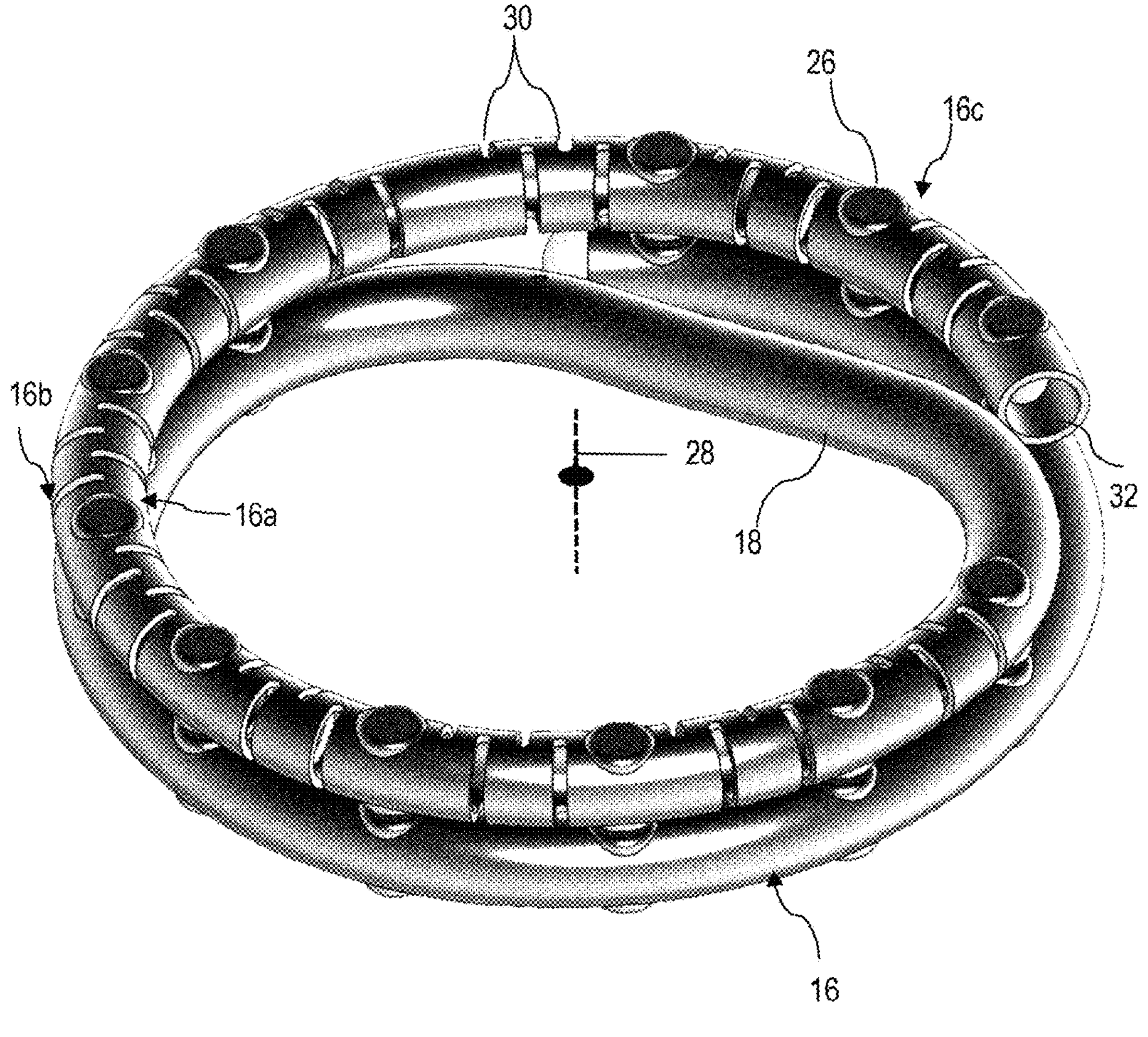
FIG. 8 is a schematic perspective view from above, similar to FIGS. 1, 5 and 6, showing a fourth embodiment of coil implant in its implantation configuration.
Figure 9:
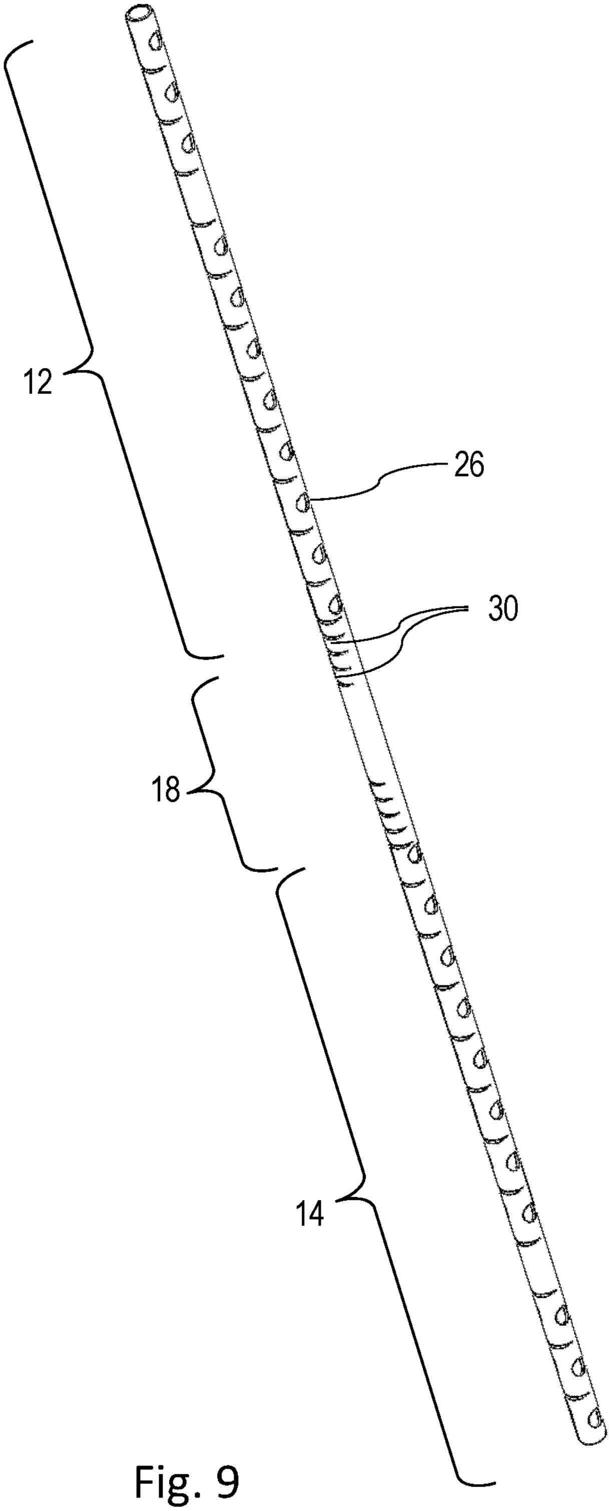
FIG. 9 is a schematic perspective view showing the implant of FIG. 5 in its stowed configuration for delivery.

Referring to FIGS. 8 and 9, in addition to, or alternative to, the apertures 26 for magnets 24, the elongate member 16 (optionally the first and second portions 12 and 14) may comprise apertures (e.g. slots) and/or cuts 30 configured for enhancing flexibility of the elongate member 16. The cuts and/or apertures 30 may, for example, be formed by laser cutting the shape-memory material of the elongate member 16.

The apertures and/or cuts 30 for flexibility are especially advantageous when the elongate member 16 is tubular and/or rodlike, and so potentially more structural and/or stiffer than would be a wire.

Optionally, the cuts and/or apertures 30 for enhancing flexibility are formed in one or more surface regions **16*a*, 16*b* selected to enhance flexibility in a plane perpendicular to a central axis of the coil in the implanted configuration. For example, the one or more surface may include one or more of: (i) a surface region 16*a* of the elongate member 16 that faces radially inwardly towards a central axis of the coil in the implantation configuration, and/or (ii) a surface region 16*b* of the elongate member 16 that faces radially outwardly away from a central axis of the coil in the implantation configuration. The apertures 16** can expand and collapse to enhance the flexibility.

With such an arrangement, one or both loops can exhibit greater flexibility in the plane of the loop, allowing the loops to conform closely in shape and allowing the magnets to align in register for optimum mutual attraction. Also, the enhanced flexibility in the mutual planes of the loops enables the coil implant to compress or elongate into an oval shape when the implant separates from the tissue walls after anastomosis creation. This can facilitate evacuation of the implant, for example, via the anus, with less risk of blockage, injury or discomfort for the patient.

The enhanced flexibility in the radial direction does not detract significantly from the stiffness of the elongate member 16 in the axial direction of the coil in the implanted configuration. This can enable the loops to be self-guided to the implanted configuration in which the loops sandwich the tissue walls, and the magnets 24 are brought sufficiently close in the axial direction for the magnetic attraction to securely clamp the tissue from either side.

In the illustrated embodiments, each portion 12, 14 defines generally a single and/or complete turn of a loop. However, in general, the portions 12, 14 and/or their respective loops, may each generally comprise one or more of: at least 0.8 of a complete turn; at least 0.9 of a complete turn; at least 1.0 complete turn; at least 1.25 complete turns; at least 1.5 complete turns, at least 1.75 complete turns, at least 1.8 complete turns; at least 1.9 complete turns, at least 2.0 complete turns, optionally at least 2.5 complete turns, optionally at least 2.8 complete turns, optionally at least 2.9 complete turns, optionally at least 3.0 complete turns.

Figure 4:
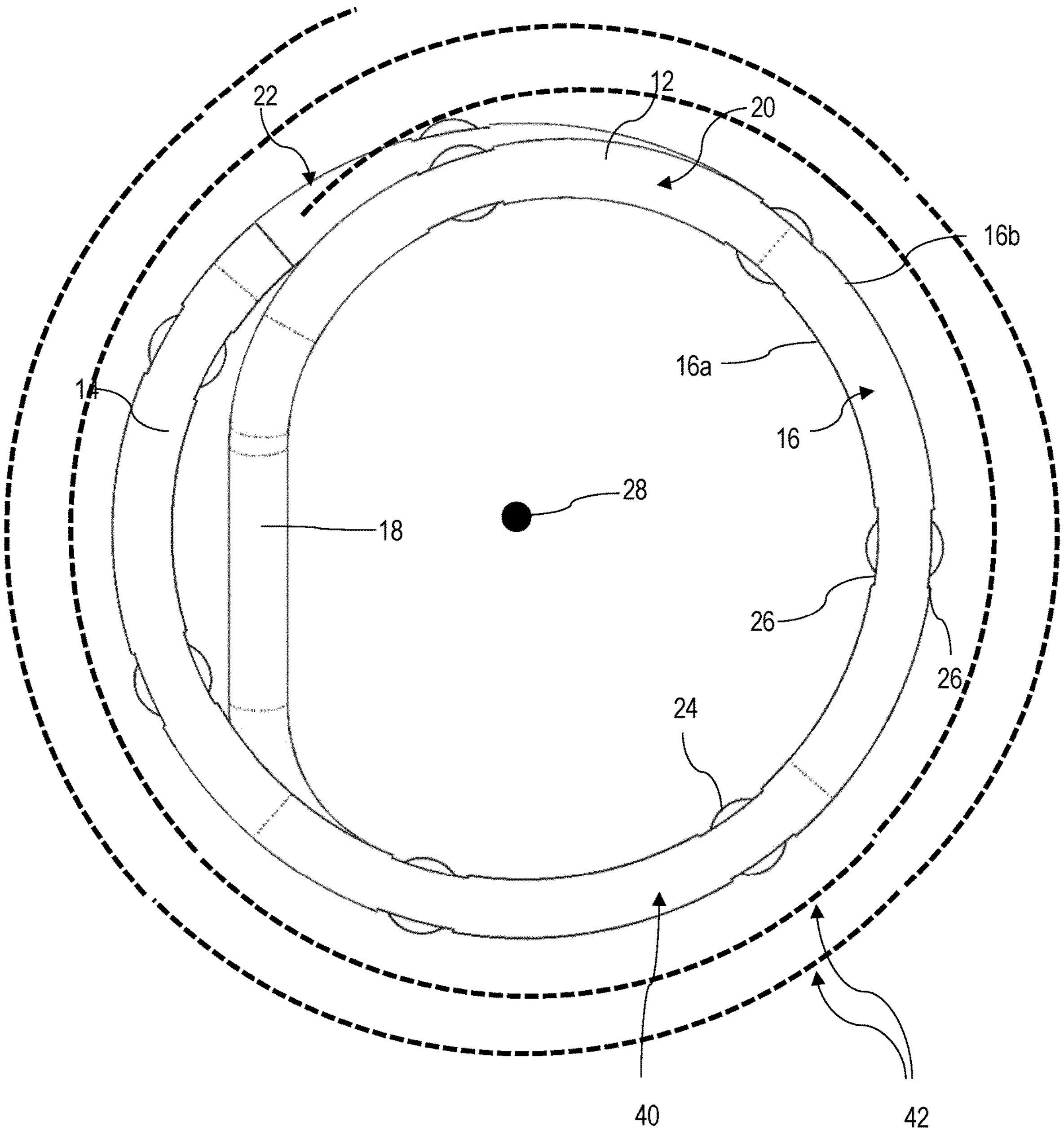
FIG. 4 is a schematic plan view of the coil implant of FIGS. 1 to 3.
Figure 5:
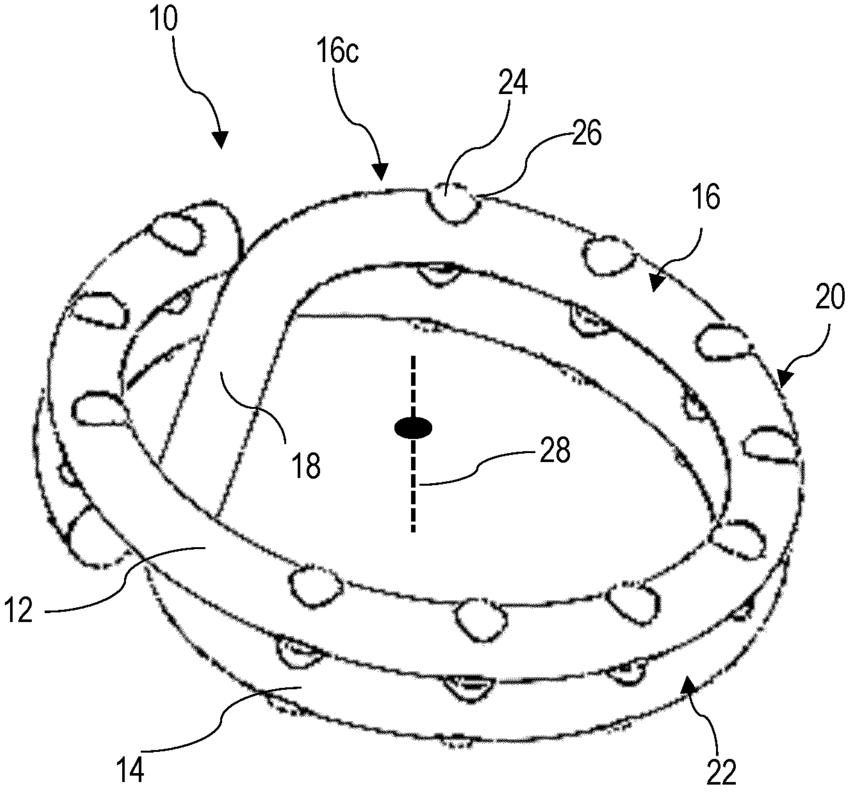
FIG. 5 is a schematic perspective view similar to FIG. 1, showing a second embodiment of coil implant in its implantation configuration.
Figure 6:
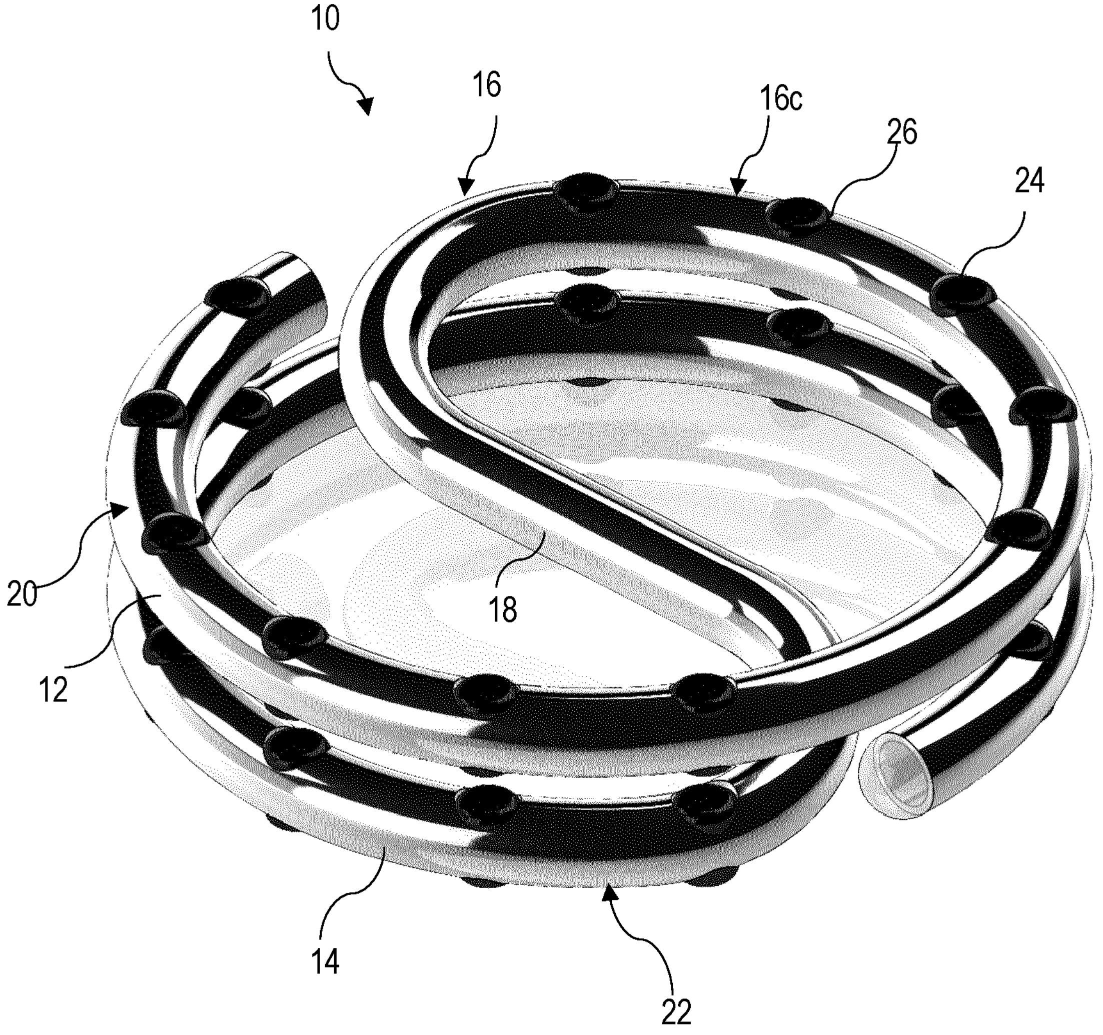
FIG. 6 is a schematic perspective view similar to FIGS. 1 and 5, showing a third embodiment of coil implant in its implantation configuration.
Figure 7:
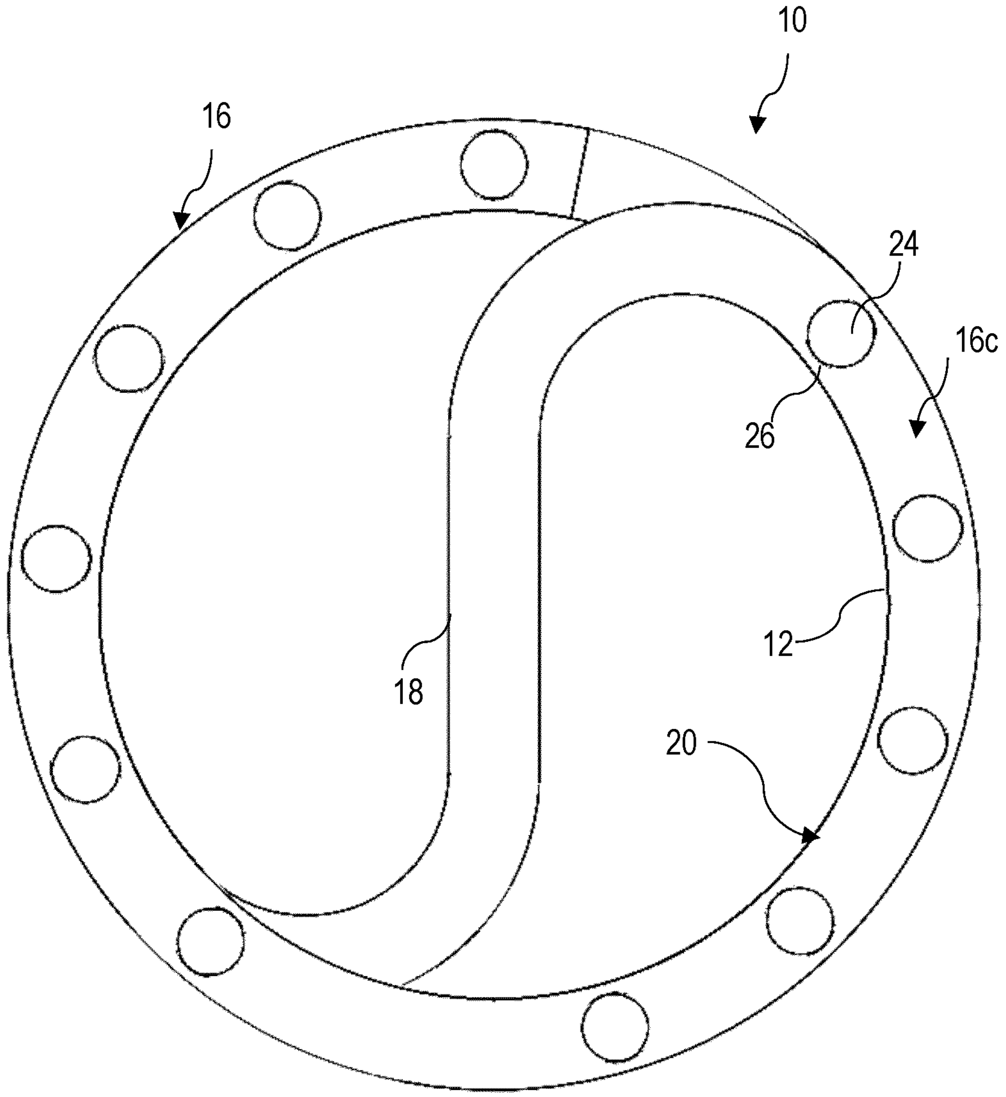
FIG. 7 is a schematic plan view of the coil implant of FIG. 6.
Figure 10:
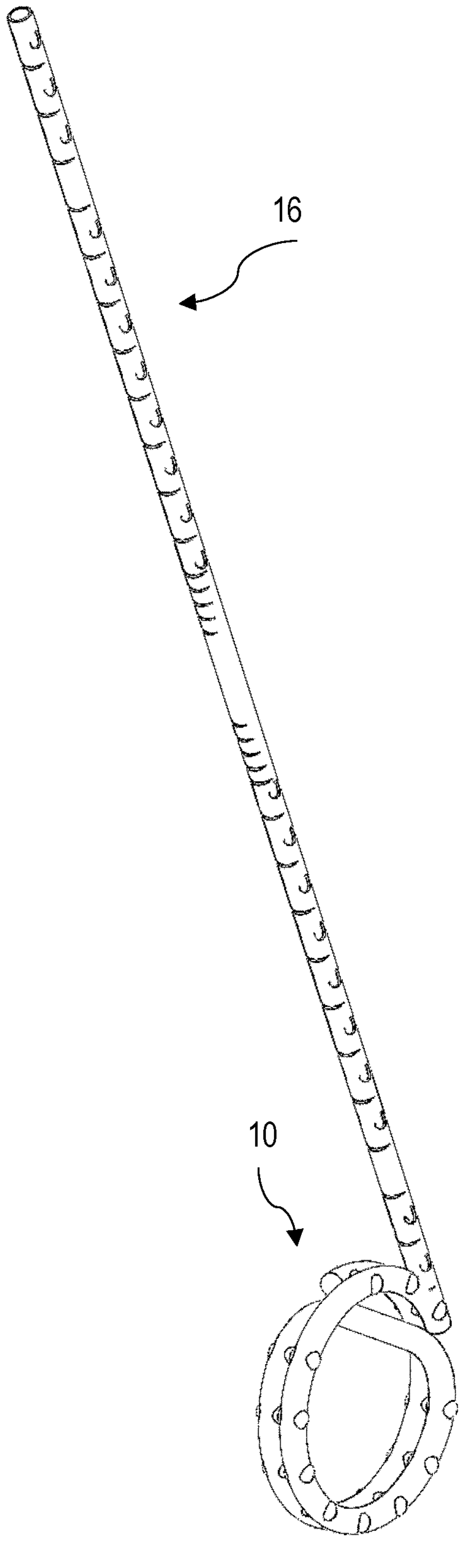
FIG. 10 is a schematic hybrid drawing combining FIGS. 5 and 9 in a single representation.

More than two turns are also envisaged per loop, for example, in a spiral shape, as illustrated by the broken line in FIG. 4, which illustrates 3 complete turns in the loop (s). However, the greater the number of turns, the longer the implant 10 when in its stowed configuration. Referring to FIG. 10, the total of the lengths of the first and second portions 12 and 14, and optionally the bridging section 18 define the length of the stowed configuration 34. For a coil implant 10 including loops 20 and 22 each with only with single turn of diameter D in the implantation configuration, the length in the stowed configuration may be seven to eight times the diameter D. The ability of the illustrated embodiments to provide an anastomosis-creation device with relatively few turns on either side of the wall tissue, can keep the device relatively compact, and also relatively short in the stowed configuration.

In some embodiments, where at least one of the first and second portions 12, 14 comprises material for more than one complete turn of the respective loop 20, 22, the respective portion may have first and second segments 40, 42 (FIG. 4). A first segment 40 may be at least partly closer to a central axis of the spiral shape than the second segment 42. The second segment 42 may be configured to provide increased flexibility and/or weaker compressive forces against the tissue compared to the first segment.

Increased flexibility may, for example, be provided by more frequent or larger cuts 30. By increasing flexibility, there is less tendency for the implant 10 to spring or jump free of the delivery device when only a small part of the implant 10 remains engaged by the delivery device. The increase in flexibility can reduce the forces urging separation of the implant 10 in the final stages of deployment.

Additionally or alternatively, weaker compression forces may be provided by using smaller and/or weaker magnets, or by increasing the distance between adjacent magnets. Alternatively, the second segment 42 may carry no magnets, and instead rely only on its connection to the first segment 40 at the inner turn of the loop to apply a compression force to the tissue.

By applying a compression force that is relatively weaker, around at least one outer turn of the spiral, than the compression force applied by an inner turn of the spiral, the compression effect on the tissue wall sections can be tailored to assist in anastomosis formation. The compression force can be concentrated at a first tissue zone corresponding to the first segment 40 of the loop, leading to tissue necrosis by which the anastomosis is created. The smaller compression force in a second tissue zone corresponding to the second segment 42 may be radially outwardly of, and surround, the first zone. The smaller compression force may press tissue wall section together in the second zone, to urge fusion of tissue as part of the healing effect, but optionally without necrosis in the second zone. This can lead to a radially thick band of joined tissue around the anastomosis.

Although the illustrated embodiments shows apparatus in the form of a coil implant, it will be appreciated that the techniques described herein may be used with other forms of device, for example, in which the first and second portions 12, 14 are constituted by separate devices (e.g. separate loop devices) on opposite sides of the tissue wall sections, and held in operative relation by magnetic attraction alone.

It will be appreciated that the foregoing description is merely illustrative of preferred embodiments, and does not limit the invention. Many modifications and improvements can be made within the principles of the invention.

The invention claimed is:

1. An apparatus for forming an anastomosis between first and second body lumen wall sections, the apparatus comprising a coil implant comprising an elongate member made of shape memory material, the elongate member being self-expanding from a stretched-out stowed configuration for introduction into the body, to an implantation configuration in which a first portion of the elongate member forms at least a first loop of the coil and a second portion of the elongate member forms at least a second loop of the coil, the elongate member comprising at least one interior cavity, the coil implant further comprising a plurality of magnets carried by the first and second portions of the elongate member, each magnet of the plurality being at least partly accommodated within the at least one interior cavity of the elongate member, the magnets arranged such that the first loop is magnetically attracted to the second loop for creating a magnetic compression anastomosis in tissue trapped between the first and second loops, wherein the elongate member further comprises a bridging section between the first and second portions, the bridging section not carrying a magnet, and wherein at least one of the first and second portions comprises a circumferential discontinuity where the respective portion bends away to form the bridging section.

2. The apparatus according to claim 1, wherein at least two magnets of the plurality of magnets are accommodated, at least partly, within the same cavity of the elongate member.

3. The apparatus according to claim 1, wherein the elongate member comprises a tube, and the cavity includes a hollow interior of the tube.

4. The apparatus according to claim 1, wherein the elongate member comprises apertures spaced apart along its length, and wherein at least some of the magnets are arranged at and/or in at least some of the apertures.

5. The apparatus according to claim 4, wherein the apertures in which the magnets are arranged are defined in: (i) a surface region of the elongate member that faces radially inwardly towards a central axis of the coil in the implantation configuration, and/or (ii) a surface region of the elongate member that faces radially outwardly away from a central axis of the coil in the implantation configuration; and/or (iii) a surface region of the elongate member facing parallel to the central axis of the coil in the implantation configuration.

6. The apparatus according to claim 1, wherein the elongate member further comprises or is provided with a plurality of cuts and/or apertures for enhancing flexibility of the elongate member.

7. The apparatus according to claim 6, wherein the cuts and/or apertures for enhancing flexibility are formed in one or more surface regions selected to enhance flexibility in a plane perpendicular to a central axis of the coil in the implanted configuration, said one or more surface regions being: (i) a surface region of the elongate member that faces radially inwardly towards a central axis of the coil in the implantation configuration, and/or (ii) a surface region of the elongate member that faces radially outwardly away from a central axis of the coil in the implantation configuration.

8. The apparatus according to claim 6, wherein at least some of the apertures and/or cuts communicate with a hollow interior of the elongate member.

9. The apparatus according to claim 1, wherein at least one of the first and second portions is configured to provide, in the implanted configuration, at least 80% of a complete turn around the axis of the coil.

10. The apparatus according to claim 1, wherein at least one of the first and second portions comprises a generally planar spiral shape of more than one turn in the implantation configuration.

11. The apparatus according to claim 10, wherein one turn has a greater rigidity than another turn in the spiral.

12. The apparatus according to claim 1, wherein the elongate member is a monolithic body.

13. The apparatus according to claim 1, wherein at least one of the first and second portions is configured to coil at least partly around an axis when transitioning from the stowed configuration to the implanted configuration.

14. The apparatus according to claim 1, wherein at least one of the first and second portions is configured to wind at least partly around an axis when transitioning from the stowed configuration to the implanted configuration.

15. The apparatus according to claim 1, wherein in the implantation configuration, the first loop is in a first plane, the second loop is in a second plane, and the bridging section extends between the first and second planes.

16. The apparatus according to claim 1, wherein in the implantation configuration, the bridging section is generally inclined with respect to the first and second portions of the elongate member.

17. The apparatus according to claim 1, wherein the bridging section is generally continuous with the first and second portions of the elongate member.

18. The apparatus according to claim 1, wherein a diameter of the elongate member is substantially the same in the first and second portions and in the bridging section, at least in the implantation configuration.

19. An apparatus for forming an anastomosis between first and second body lumen wall sections, the apparatus comprising a coil implant comprising an elongate member made of shape memory material, the elongate member being self-expanding from a stretched-out stowed configuration for introduction into the body, to an implantation configuration in which a first portion of the elongate member forms at least a first loop of the coil and a second portion of the elongate member forms at least a second loop of the coil, the elongate member comprising at least one interior cavity, the coil implant further comprising a plurality of magnets carried by the first and second portions of the elongate member, each magnet of the plurality being at least partly accommodated within the at least one interior cavity of the elongate member, the magnets arranged such that the first loop is magnetically attracted to the second loop for creating a magnetic compression anastomosis in tissue trapped between the first and second loops, wherein the elongate member comprises apertures spaced apart along its length, and wherein at least some of the magnets are arranged at and/or in at least some of the apertures, and wherein the apertures in which the magnets are arranged are defined in: (i) a surface region of the elongate member that faces radially inwardly towards a central axis of the coil in the implantation configuration, and/or (ii) a surface region of the elongate member that faces radially outwardly away from a central axis of the coil in the implantation configuration; and/or (iii) a surface region of the elongate member facing parallel to the central axis of the coil in the implantation configuration.

20. An apparatus for forming an anastomosis between first and second body lumen wall sections, the apparatus comprising a coil implant comprising an elongate member made of shape memory material, the elongate member being self-expanding from a stretched-out stowed configuration for introduction into the body, to an implantation configuration in which a first portion of the elongate member forms at least a first loop of the coil and a second portion of the elongate member forms at least a second loop of the coil, the elongate member comprising at least one interior cavity, the coil implant further comprising a plurality of magnets carried by the first and second portions of the elongate member, each magnet of the plurality being at least partly accommodated within the at least one interior cavity of the elongate member, the magnets arranged such that the first loop is magnetically attracted to the second loop for creating a magnetic compression anastomosis in tissue trapped between the first and second loops, wherein the elongate member further comprises or is provided with a plurality of cuts and/or apertures for enhancing flexibility of the elongate member, and wherein the cuts and/or apertures for enhancing flexibility are formed in one or more surface regions selected to enhance flexibility in a plane perpendicular to a central axis of the coil in the implanted configuration, said one or more surface regions being: (i) a surface region of the elongate member that faces radially inwardly towards a central axis of the coil in the implantation configuration, and/or (ii) a surface region of the elongate member that faces radially outwardly away from a central axis of the coil in the implantation configuration.

* * * * *